United States Patent
Läubli et al.

(10) Patent No.: US 11,712,660 B2
(45) Date of Patent: Aug. 1, 2023

(54) DIALYSIS CELL FOR SAMPLE PREPARATION FOR A CHEMICAL ANALYSIS METHOD

(71) Applicant: METROHM AG, Herisau (CH)

(72) Inventors: Markus Läubli, Herisau (CH); Wolfgang Frenzel, Berlin (DE); Inga Markeviciute, Berlin (DE); Daniel Abderhalden, Waldkirch (CH)

(73) Assignee: Metrohm AG, Herisau (CH)

( * ) Notice: Subject to any disclaimer, the term of this patent is extended or adjusted under 35 U.S.C. 154(b) by 530 days.

(21) Appl. No.: 16/637,804

(22) PCT Filed: Aug. 10, 2018

(86) PCT No.: PCT/EP2018/071821
§ 371 (c)(1),
(2) Date: Feb. 10, 2020

(87) PCT Pub. No.: WO2019/030404
PCT Pub. Date: Feb. 14, 2019

(65) Prior Publication Data
US 2020/0215488 A1    Jul. 9, 2020

(30) Foreign Application Priority Data
Aug. 11, 2017   (EP) .................................. 17185845

(51) Int. Cl.
*B01D 61/24* (2006.01)
*B01D 61/28* (2006.01)
(Continued)

(52) U.S. Cl.
CPC ........... *B01D 61/243* (2013.01); *B01D 61/28* (2013.01); *B01D 63/087* (2013.01); *B01D 71/14* (2013.01);
(Continued)

(58) Field of Classification Search
CPC .... B01D 61/243; B01D 61/28; B01D 63/087; B01D 71/14; B01D 71/34; B01D 71/50;
(Continued)

(56) References Cited

U.S. PATENT DOCUMENTS 4,311,789 A     1/1982  Nylen et al.
4,419,237 A  *  12/1983 Esmond ................. B01D 61/28
                                                210/321.77
(Continued)

FOREIGN PATENT DOCUMENTS

DE    102008017083 A1    10/2009
EP        0 180 321 A2    5/1986
(Continued)

OTHER PUBLICATIONS

De Borba et al., "On-line dialysis as a sample preparation technique for ion chromatography", Journal of Chromatography A, 919, (2001), pp. 59-65 See International Search.
(Continued)

*Primary Examiner* — Krishnan S Menon
(74) *Attorney, Agent, or Firm* — Finch & Maloney PLLC

(57) ABSTRACT

The invention relates to a dialysis cell for sample preparation for a chemical analysis method, in particular for ion chromatography. The dialysis cell comprises a donor channel and an acceptor channel extending parallel thereto. The donor channel and the acceptor channel are separated from each other by a selectively permeable dialysis membrane. In particular, an analyte that is dissolved in a donor solution in the donor channel can enter through the dialysis membrane into the acceptor solution in the acceptor channel. The acceptor channel has at least in some sections a volume that is smaller than the volume of the donor channel extending parallel thereto. Acceptor and donor channels are formed from half-cells, between which the dialysis membrane is
(Continued)

arranged, wherein the donor channel and the acceptor channel are designed in each case as a recess in a contact surface of one of the half-cells with the dialysis membrane.

10 Claims, 8 Drawing Sheets

(51) Int. Cl.
| | |
|---|---|
| *B01D 63/08* | (2006.01) |
| *B01D 71/14* | (2006.01) |
| *B01D 71/34* | (2006.01) |
| *B01D 71/50* | (2006.01) |
| *G01N 1/34* | (2006.01) |
| *G01N 30/14* | (2006.01) |
| *G01N 1/40* | (2006.01) |
| *G01N 30/02* | (2006.01) |
| *A61M 1/16* | (2006.01) |
| *A61M 1/14* | (2006.01) |

(52) U.S. Cl.
CPC ............ *B01D 71/34* (2013.01); *B01D 71/50* (2013.01); *G01N 1/34* (2013.01); *G01N 30/14* (2013.01); *A61M 1/14* (2013.01); *A61M 1/16* (2013.01); *B01D 2311/26* (2013.01); *B01D 2313/28* (2013.01); *B01D 2313/30* (2013.01); *G01N 2001/4016* (2013.01); *G01N 2030/027* (2013.01); *G01N 2030/146* (2013.01)

(58) Field of Classification Search
CPC ............ B01D 2311/26; B01D 2313/28; B01D 2313/30; G01N 1/34; G01N 30/14; G01N 2001/4016; G01N 2030/027; G01N 2030/146; G01N 30/96; A61M 1/14; A61M 1/16
See application file for complete search history.

(56) References Cited

U.S. PATENT DOCUMENTS

| | | |
|---|---|---|
| 4,491,011 A | 1/1985 | Nordmeyer et al. |
| 4,837,157 A | 6/1989 | Turnell et al. |
| 5,861,097 A | 1/1999 | Schäfer et al. |
| 9,103,780 B2 | 8/2015 | Ohira et al. |
| 2005/0191759 A1 | 9/2005 | Pedersen-Bjergaard et al. |
| 2006/0024839 A1 | 2/2006 | Petropavlovskikh et al. |
| 2011/0163023 A1 | 7/2011 | Kreusch et al. |
| 2016/0056030 A1 | 2/2016 | Krogh et al. |

FOREIGN PATENT DOCUMENTS

| | | |
|---|---|---|
| EP | 0 820 804 A1 | 1/1998 |
| WO | 2005/119245 A1 | 12/2005 |

OTHER PUBLICATIONS

International Search Report Corresponding to PCT/EP2018/071821 dated Mar. 8, 2019.
Written Opinion Corresponding to PCT/EP2018/071821 dated Mar. 8, 2019.
European Office Action corresponding to application No. EP 18749831.6 dated Jun. 7, 2022.

* cited by examiner

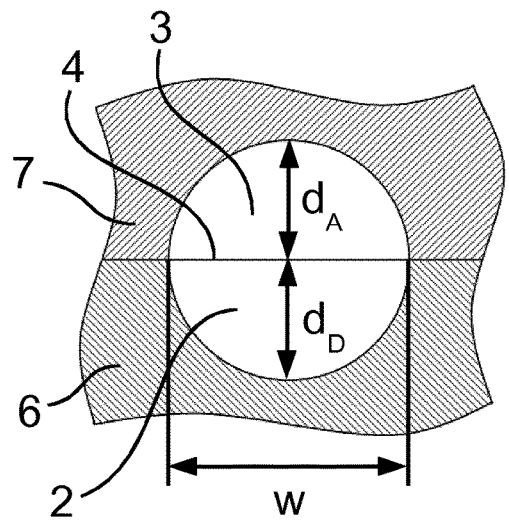
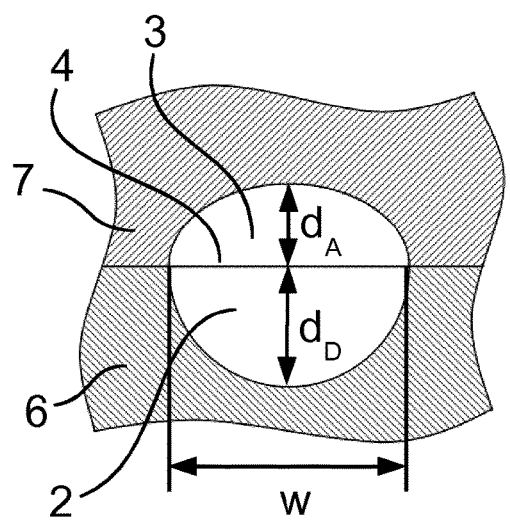
Fig. 2　　　　　　　　Fig. 3
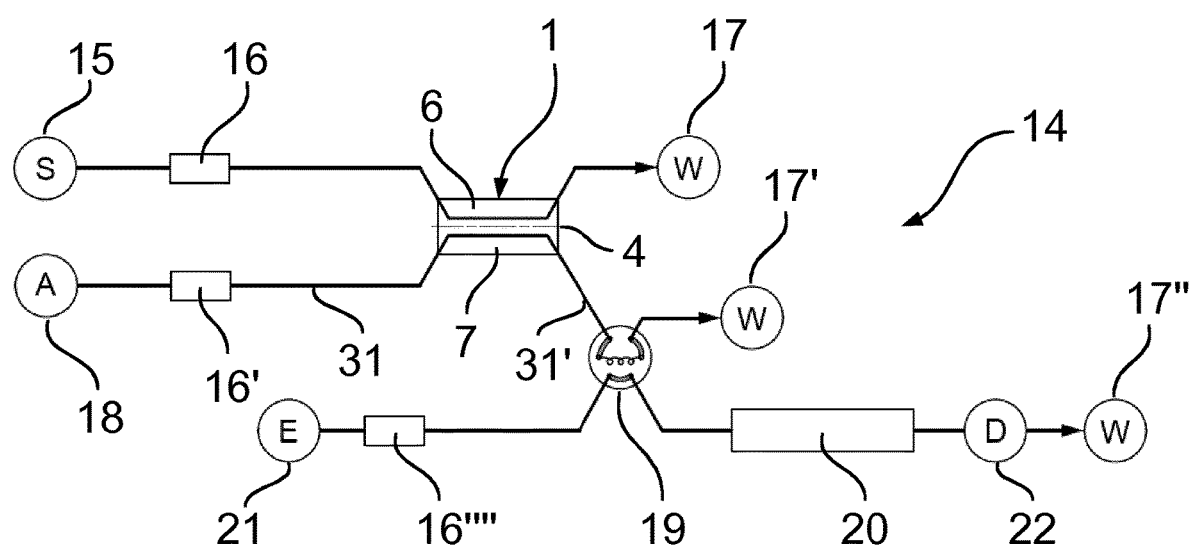
Fig. 4

DIALYSIS CELL FOR SAMPLE PREPARATION FOR A CHEMICAL ANALYSIS METHOD

This application is a National Stage completion of PCT/EP2018/071821 filed Aug. 10, 2018, which claims priority from European patent application serial no. 17185845.9 filed Aug. 11, 2017.

FIELD OF THE INVENTION

The present invention relates to a dialysis cell for sample preparation for a chemical analytical, to a device for sample preparation, to the use of a dialysis cell and to the use of a membrane as dialysis membrane in such a dialysis cell. The present invention further relates to an analytical system comprising a dialysis cell.

BACKGROUND OF THE INVENTION

In many chemical analytical methods, it is necessary to subject a sample to a preparation procedure before an actual analysis can be carried out. For example, samples for analysis by means of ion chromatography frequently contain matrix constituents, which are corrosive or can lead to precipitates, in addition to the ions to be analyzed, the analyte(s). Said matrix constituents sometimes make the analysis difficult or even impossible. Furthermore, heavily contaminated samples can damage the separation column or lead to a significant reduction in its service life. Accordingly, an absolute requirement of numerous analytical applications is a suitable sample preparation procedure. While all sample preparation steps have traditionally been carried out manually, so-called inline sample preparation techniques have gained acceptance in recent years. These make it possible to completely automate the preparation method.

For instance, EP 0 820 804 A1 describes an inline dialysis used especially for ion chromatography. Said dialysis method is carried out by means of a dialysis cell comprising a donor channel and a parallelly running acceptor channel. Arranged between these two channels is a selectively permeable dialysis membrane. The dialysis is carried out as a so-called stopped-flow dialysis. This involves a liquid sample, also called a donor solution, being continuously conducted through the donor channel. At the same time, a fluid flow of an acceptor solution through the acceptor channel is stopped for a certain period. The concentration gradient between the donor solution and the acceptor solution leads to a diffusion of the analytes from the donor solution into the acceptor solution. After a concentration equilibrium has been substantially reached, the acceptor solution is supplied to an ion-chromatography separation procedure.

The time span from the stopping of the acceptor flow up to the end of the dialysis, which typically occurs when the acceptor solution is forwarded from the dialysis cell, is referred to as dialysis time $t_D$.

The recovery rate R is defined as the ratio of the analyte concentration in the acceptor channel to the analyte concentration in the donor channel at the end of the dialysis time $t_D$. The recovery rate R typically rises in a strictly monotonous manner with increasing dialysis time $t_D$.

The equilibration time $t_A$ refers to the time in which the analyte concentration in the acceptor channel has substantially reached that in the donor channel. In the present context, the equilibration time to corresponds to the period of dialysis, after which the relative change in the analyte concentration in the acceptor channel is less than 2%/min for the first time.

The technique described separates not only particles from the analyte(s), but also colloids, oil constituents and large molecules. Protein-containing samples in particular can thereby be directly processed by means of ion chromatography. This saves time-consuming manual work steps, such as, for example, a precipitation of the proteins by means of Carrez reagent. Even if samples are contaminated with particles and a filtration procedure cannot be applied because of clogging filters, inline dialysis is a practical sample preparation procedure.

Although this sample preparation technique has many advantages, there is generally the problem that the dialysis is the rate-limiting step of the analytical process. This is disadvantageous especially in the case of a serial processing of many samples, since the method becomes time-consuming and cost-intensive as a result of the sample preparation. Furthermore, there is the problem that a partial breakthrough of matrix impurities through the dialysis membrane can occur in the case of heavily contaminated samples. A further disadvantage is the comparatively high sample expenditure in stopped-flow dialysis.

U.S. Pat. Nos. 4,311,789 and 4,491,011 disclose analyzers connected to an upstream dialysis unit. In both cases, the dialysis cell is designed such that a complex fluid medium, specifically blood, is guided through a channel, said channel containing a further fluid guide formed from a selectively permeable membrane in full or in part, for example a fiber or capillary composed of a selectively permeable membrane. The acceptor solution is provided in said further fluid guide. When the volume of the acceptor channel has, at least sectionally, a volume $V_A$ which is smaller than a parallelly running volume $V_D$ of the donor channel, this can have advantageous effects on the equilibration time. However, the known dialysis cells operate without suitable control of the pressure difference between donor channel and acceptor channel. Pressure gradients in the donor channel and/or acceptor channel lead to undesired filtration. The buildup of a filter cake especially in the case of particle-loaded matrices changes the permeability of the dialysis membrane. The change in permeability may even be different in each case for the individual analytes. As a result, the equilibration time $t_A$ is influenced in an unpredictable manner and is difficult to control.

SUMMARY OF THE INVENTION

It is therefore an object of the present invention to overcome the abovementioned disadvantages in the prior art. More particularly, it is an object of the present invention to shorten the equilibration time $t_A$ and to thus achieve an altogether higher sample throughput. Furthermore, the problem addressed by the present invention is that of achieving a better removal of the analyte(s) from the matrix in the case of heavily contaminated samples. Moreover, it is an object of the present invention to provide a device and a method for sample preparation by means of dialysis, by means of which a reliable and precise equilibration within a controllable equilibration time $t_A$ is made possible.

These objects are achieved by a dialysis cell for sample preparation for a chemical analytical method, especially for ion chromatography, having the features in claim 1. The dialysis cell comprises a donor channel and a parallelly running acceptor channel. The donor channel and the acceptor channel are separated from one another by a selectively permeable dialysis membrane when used as intended. This means that, in particular, an analyte dissolved in a donor solution in the donor channel can get into the acceptor solution in the acceptor channel through the dialysis membrane. The acceptor channel has, at least sectionally, a volume $V_A$ which is smaller than a parallelly running volume $V_D$ of the donor channel.

It has been found that such an asymmetrical structure of the dialysis cell can markedly lower the equilibration times $t_A$. This leads to shorter dialysis times $t_D$ and thus to an altogether higher sample throughput, and this is associated with a distinct saving of time and costs. Furthermore, shorter dialysis times $t_D$ reduce the period of time during which the dialysis membrane is in contact with the sample matrix. As a result, the breakthrough of matrix impurities can be significantly reduced. Moreover, the dialysis can be carried out with a distinctly smaller sample volume.

The dialysis cell according to the invention comprises two half-cells, between which the selectively permeable dialysis membrane is arranged. The donor channel and the acceptor channel are formed as, in each case, an indentation in a contact surface of one of the half-cells with the dialysis membrane. This structure of the dialysis cell has proved to be particularly robust, cost-effective in manufacturing and user-friendly with respect to operation and maintenance.

Moreover, the volumes of both half-cells are known and constant in the case of such a structure. By suitably choosing the amount/flow rate of the supplied and removed donor liquid or acceptor liquid, it is possible to avoid a positive pressure or negative pressure in one of the half-cells. Such a positive pressure or negative pressure leads to filtration, which can have an interfering effect on the concentration equilibrium of the analytes in the donor solution and acceptor solution that is reached as a consequence of diffusion. For example, filtrate can pass over into the acceptor channel in the case of a positive pressure in the donor channel.

The pressure-free dialysis, i.e., the dialysis in the absence of a pressure gradient within the dialysis cell, proves advantageous especially when donor liquids based on changing media or matrices are to be subjected to the dialysis. In the case of an unchanging matrix, as exists in the dialysis and/or analysis of blood serum in medical applications for example, the flow rate and thus the pressure can be appropriately adjusted on the basis of empirical values with corresponding effort, without the precision of the analytical values being excessively compromised as a result. In the case of changing matrices, as frequently occur in ion analysis by contrast, a pressure difference leads to uncontrollable and unpredictable dialysis times or equilibration times.

The control of pressure is additionally supported when the dialysis is carried out in a stopped-flow method.

In a preferred embodiment of the present invention, the acceptor channel has, on at least 50%, preferably at least 70% and more preferably at least 90% of its length, a volume $V_A$ which is smaller than a parallelly running volume $V_D$ of the donor channel. In a further preferred embodiment of the present invention, the acceptor channel has, on its entire length, a volume $V_A$ which is smaller than a parallelly running volume $V_D$ of the donor channel.

The acceptor channel can have, at least sectionally, a volume per unit of length $V_A/L$ of from 0.005 mm$^3$/mm to 2.0 mm$^3$/mm, preferably from 0.020 mm$^3$/mm to 1.5 mm$^3$/mm and more preferably from 0.10 mm$^3$/mm to 1.0 mm$^3$/mm. The donor channel can have, at least sectionally, a volume per unit of length $V_D/L$ of from 0.25 mm$^3$/mm to 3.5 mm$^3$/mm, preferably from 0.30 mm$^3$/mm to 3.0 mm$^3$/mm and more preferably from 0.35 mm$^3$/mm to 2.0 mm$^3$/mm. At the same time, the donor channel and the acceptor channel usually each have a length of from 10 mm to 1000 mm, preferably from 20 mm to 500 mm and more preferably from 100 mm to 300 mm.

It has been found that such dimensioning of the donor channel and/or the acceptor channel is advantageous especially in applications in ion chromatography. Firstly, distinctly shorter equilibration times $t_A$ can be achieved as a result. Secondly, these dimensions ensure that the substance amount of analyte that is supplied to the separation column is within the detection limits of a customary ion chromatography system. With respect to the donor channel, these dimensions furthermore ensure that it does not become clogged even in the case of samples which are heavily contaminated, especially with particles.

The selectively permeable dialysis membrane can have a pore size of from 0.01 μm to 1.0 μm, preferably from 0.02 μm to 0.5 μm and more preferably from 0.05 μm to 0.2 μm. Since a required recovery rate R is reached more rapidly as a result of the asymmetrical structure, according to the invention, of the dialysis cell with the same dialysis membrane, it is also possible to use a finer-pored dialysis membrane for a given analytical application without having to accept a longer equilibration time $t_A$. As a result, a better separation of the matrix from the analyte(s) can be achieved especially in the case of heavily contaminated samples.

The selectively permeable dialysis membrane can consist of a material selected from a list consisting of cellulose acetate, cellulose nitrate, polyvinylidene fluoride, polycarbonate, mixed cellulose ester, cellulose hydrate and regenerated cellulose. Preferably, the material is selected from a list consisting of polyvinylidene fluoride, polycarbonate and mixed cellulose ester, or polyamide. These membrane materials have proved to be particularly advantageous especially in the separation of metal cations and inorganic anions.

The donor channel and the acceptor channel can be linear, spiral or meandering. This allows a particularly compact design of the dialysis cell in relation to the channel length.

The cross section through the donor channel and/or the acceptor channel can be the shape of a circle segment, especially semicircular, semielliptical, square or rectangular. These channel geometries have proved to be particularly advantageous both with respect to the manufacture of the half-cells and with regard to their performance characteristics.

However, it is particularly preferred when the cross section of the donor channel is semicircular. The semicircular design means that the high-molecular-weight constituents, for example fats or proteins, can flow unhindered, while the exposure area of the donor solution toward the dialysis membrane is maximal.

Moreover, it is particularly preferred when the cross section through the acceptor channel is, at least sectionally, a rectangle having rounded corners on the side facing away from the dialysis membrane. Rounded corners are understood here to mean the sections which connect the section of the acceptor channel that is opposite the dialysis membrane to the lateral boundaries of the acceptor channel that are attached to the dialysis membrane. Said sections are arc-shaped in cross section and have a radius of curvature r between 0.05 and 1 mm, preferably between 0.1 and 0.8 mm and particularly preferably between 0.2 and 0.4 mm. Additionally or alternatively, the ratio of the side bounded by the dialysis membrane to the depth of the rectangle is preferably from 80:1 to 10:1, particularly preferably from 40:1 to 15:1 and particularly preferably from 25:1 to 20:1.

By choosing dimensions mentioned above, the donor liquid per section of the cell faces a smallest possible volume of acceptor liquid, with nevertheless a large contact surface between acceptor liquid and dialysis membrane. In other words, the acceptor channel has a volume $V_A$ which is minimized in comparison with the parallelly running volume section $V_D$ of the donor channel, and this shortens the equilibration time $t_A$.

In comparison with nonrounded corners, the rounded corners prevent the contamination of the cell due to accumulation of acceptor liquid. Such contamination typically comes about as a result of the slowed flow velocity near the channel wall, which would be accentuated in nonrounded corners. The problem of accumulation of slowly flowing acceptor liquid also arises if the radius of curvature that is selected is too small. By contrast, if the radius of curvature that is selected is too large, there is the risk that the dialysis membrane, which can swell up in aqueous solution up to 0.15 mm in thickness, contacts the walls and/or the base of the indentation of the half-cell and thus obstructs the flow through the half-cell. It is therefore preferred that the radius of curvature is between 0.05 and 1 mm, preferably between 0.1 and 0.8 mm and particularly preferably between 0.2 and 0.4 mm.

Furthermore, it is preferred that the dialysis cell is configured such that at least one, preferably multiple support elements are formed in the acceptor channel, which support elements space the dialysis membrane from the side of the acceptor channel that faces away from the dialysis membrane. Preferably, the support elements have a height corresponding to the depth of the acceptor channel. Preferably, the support elements are cylindrically symmetrical with a support top-edge diameter between 5 and 500 µm, preferably between 10 and 200 µm and particularly preferably between 30 and 60 µm. The cross-sectional geometry of the supports can, however, also deviate from cylindrical symmetry. Preferably, the area, i.e., the cross-sectional area, of the support decreases from the top edge on the membrane side. Preferably, the support elements are distributed over the width of the acceptor channel in a regular pattern; particularly preferably, a row of support elements is arranged in the middle of the acceptor channel. Preferably, the distances between every two adjacent supports and/or between a support and the directly adjacent top edge of the channel are always the same.

A function of the at least one support element is that the volume of the channel on the acceptor side is kept constant and is not reduced, for instance as a consequence of sagging of the dialysis membrane under gravity or under pressure. In principle, support elements can also be mounted on the donor side in order to prevent a volume reduction on the donor side, for instance as a consequence of sagging of the dialysis membrane under gravity or under pressure in the direction of the donor channel. Since the acceptor channel has, according to the invention, a smaller volume $V_A$ in comparison with the parallelly running volume $V_D$ of the donor channel, the relative effect of a sagging action in the acceptor channel is, however, greater and a potentially resultant obstruction of flow more drastic than on donor side.

The shape and number of the support elements is chosen such that, firstly, the stability of the device is ensured and, secondly, the flow of the fluid through the channel is obstructed as little as possible and, in addition, as little membrane area as possible is covered. Suitable for this purpose are, in particular, truncated-cone shapes, or support elements curved concavely on the surface side.

Preferably, the support elements are integrally formed with the half-cell. Preferably, the support elements are produced by milling, injection molding, hot stamping or 3D printing.

The present invention moreover provides a device for sample preparation for a chemical analytical method in a dialysis process, especially for chromatography, comprising a dialysis cell as described above, characterized in that the donor circuit has a first pump device which conveys the donor liquid to the dialysis cell and has a second pump device which conveys the donor liquid away from the dialysis cell. Additionally or alternatively, the acceptor circuit has a first pump device which conveys the acceptor liquid to the dialysis cell and has a second pump device which conveys the acceptor liquid away from the dialysis cell.

The two pumps at a time per fluid circuit can be adjusted to the same conveyed amounts per unit of time and can thereby ensure unchanging pressure in the particular half-cell, acceptor half-cell or donor half-cell.

If, in donor and acceptor circuits, only one pump is used in each case, a shut-off element, for example a valve, which stops the flow-through is required. This can achieve the stopped-flow condition for the dialysis.

The first pump device and the second pump device of the donor circuit are preferably combined in a two-channel pump, preferably a peristaltic two-channel pump. Additionally or alternatively, the first pump device and the second pump device of the acceptor circuit are preferably combined in a two-channel pump, preferably a peristaltic two-channel pump.

The use of two-channel pumps have the advantage that the volume of donor liquid or acceptor liquid that is supplied to the dialysis cell and the volume of donor liquid or acceptor liquid that is removed from the dialysis cell is always the same, since the same stroke movement conveys the donor liquid or acceptor liquid. The supply of liquid into the particular half-cell and the removal of liquid from the particular half-cell are automatically synchronized.

It is particularly preferred that the first and the second peristaltic two-channel pump are controllable such that they are operated independently of one another. Typically, only the first peristaltic pump is operated during the dialysis time $t_D$, with the result that the donor liquid flows continuously, whereas the acceptor liquid is held in the acceptor channel. Preferably, after expiration of the equilibration time $t_A$, the first peristaltic pump is stopped and only the second peristaltic pump is operated, with the result that the acceptor liquid flows, whereas the donor liquid is held in the donor channel.

Such controllability has the advantage that a negative pressure or positive pressure, which could lead to undesired filtration, can be prevented in either of the half-cells.

Preferably, a first capillary which connects, preferably via the second pump device, an acceptor solution container to the acceptor channel and/or a second capillary which connects, preferably via the first pump device, the acceptor channel to an injection device, especially for injection onto a chromatography column, is/are designed such that the diameter of the capillary comprises at most 0.5 mm, preferably at most 0.25 mm.

The diameter chosen ought to be small in order to limit diffusion of the analyte(s) during the transfer operation. If the diffusion proceeds too rapidly along the capillary, the maximum attainable recovery rate R is reduced, which effect ought to be curbed by use of capillaries having a small diameter. For the same reason, the transfer rate is preferably also minimized, and this in turn is promoted by a small capillary diameter.

The present invention furthermore provides for the use of a dialysis cell as described above for sample preparation in a chemical analytical method, especially selected from a list consisting of ion chromatography (IC), high-performance liquid chromatography (HPLC), capillary electrophoresis (CE) and mass spectrometry (MS).

The present invention provides, in a further aspect, for the use of a membrane as dialysis membrane in a dialysis cell as described above for sample preparation for a chemical analytical method, especially selected from a list consisting of ion chromatography (IC), high-performance liquid chromatography (HPLC), capillary electrophoresis (CE) and mass spectrometry (MS).

It is, however, self-evident that coupling techniques such as IC-MS, HPLC-MS or CE-MS can also be used in the context of the present invention.

The two abovementioned uses can comprise the following steps:
providing an acceptor solution;
introducing a certain amount of the acceptor solution into the acceptor channel or into an acceptor circuit containing the acceptor channel;
holding the certain amount of the acceptor solution in the acceptor channel or in the acceptor circuit containing the acceptor channel;
providing a donor solution containing at least one analyte; passing the donor solution through the donor channel, the result being that the at least one analyte present in the donor solution gets into the acceptor solution through the dialysis membrane.

In the process, fresh donor solution is conducted through the donor channel at least until the concentration of the at least one analyte in the acceptor solution is at least 90%, preferably at least 95% and more preferably at least 99% of the concentration of the at least one analyte in the donor solution.

At the point in time in which the concentration of the analyte in the acceptor solution reaches the predefined threshold, the following steps are then carried out:
holding the donor solution in the donor channel (2) or in a donor circuit containing the donor channel;
discharging the acceptor solution and supplying the acceptor solution to an analytical device, especially selected from a list consisting of an ion chromatography device (IC), a device for high-performance liquid chromatography (HPLC), a capillary electrophoresis device (CE) and a mass spectrometry device (MS).

Holding the donor solution in the donor channel (2) or in a donor circuit containing the donor channel while discharging the acceptor solution has the advantage that, even during the transfer of the acceptor solution to the analytical device, there are no pressure differences between the donor channel and the acceptor channel, for instance as a consequence of nonsynchronous switching of the pumps respectively situated on the donor circuit and acceptor circuit. This ensures that there is no undesired filtration which could distort the equilibrium achieved.

In the process, fresh donor solution can be continuously conducted through the donor channel. The flow rate of the donor solution through the donor channel can be within a range of from 0.01 ml/min to 10.0 ml/min, preferably from 0.05 ml/min to 5.0 ml/min and by preference from 0.10 ml/min to 1.0 ml/min. These flow rates have proved effective with respect to the customarily observed rate of mass transfer in such a dialysis.

The present invention furthermore provides an analytical system, especially a system selected from a list consisting of an ion chromatography system (IC), a system for high-performance liquid chromatography (HPLC), a capillary electrophoresis system (CE) and a mass spectrometry system (MS) or a combination of such systems, comprising a dialysis cell as described above.

BRIEF DESCRIPTION OF THE DRAWINGS

Further advantages and individual features of the invention are apparent from the following description of an exemplary embodiment and from the drawings.

Shown schematically are:

FIG. 2: Cross-sectional view of a dialysis cell from the prior art;

FIG. 3: Cross-sectional view of a dialysis cell according to the invention;

FIG. 4: Ion chromatography system (IC) comprising a dialysis cell according to the invention;

DETAILED DESCRIPTION OF THE PREFERRED EMBODIMENTS

Figure 1:
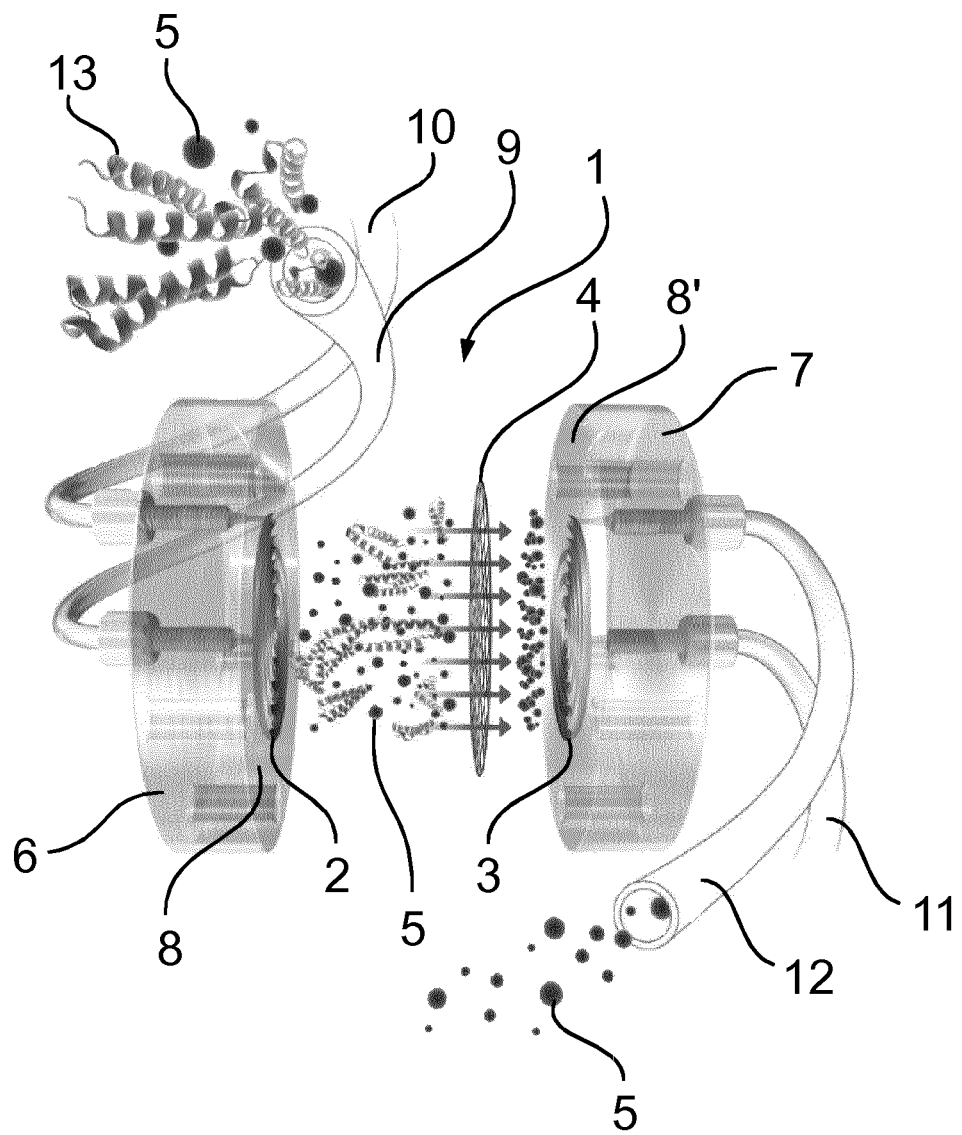
FIG. 1: Exploded perspective view of a dialysis cell according to the invention.

As is evident from FIG. 1, one embodiment of a dialysis cell 1 according to the invention consists of two half-cells 6 and 7, between which a selectively permeable dialysis membrane 4 is arranged. On their contact surfaces 8, 8' with the dialysis membrane 4, the half-cells 6 and 7 each have a spiral indentation which forms the donor channel 2 and the acceptor channel 3, respectively. The donor channel 2 is connected to a supply line 9, via which a sample can be supplied. Furthermore, the donor channel 2 is connected to a discharge line 10, by means of which the sample can be discharged after passing through the dialysis cell 1 and can be supplied usually to a disposal point 17. The acceptor channel 3 as well is connected to a supply line 11 and a discharge line 12. The supply line 11 and the discharge line 12 of the acceptor channel 3 can be united to form an acceptor circuit. The sample solution conducted through the donor channel 2 contains at least one analyte, which is depicted here symbolically as metal ion 5, and also matrix molecules, which are depicted here symbolically as proteins 13. The metal ions 5 can cross the selectively permeable dialysis membrane 4 (cf. arrows), whereas the proteins 13 are held back. As a result, a sample containing metal ions 5 can be treated, for example for ion chromatography.

FIG. 2 shows a cross section through a congeneric dialysis cell from the prior art. It can be seen that the donor channel 2 and the acceptor channel 3 have an identical width w. Moreover, the depth $d_D$ of the donor channel is also identical to the depth $d_A$ of the acceptor channel. By contrast, FIG. 3 depicts a cross section of a dialysis cell according to the invention, which cross section corresponds to FIG. 2. Both the donor channel 2 and the acceptor channel 2 still have the width w. Also, the depth of the donor channel $d_D$ is identical with respect to the example as per FIG. 2. However, the acceptor channel has a reduced depth $d_A$. It is self-evident that the acceptor channel 3 thus has, in the region of the sectional plane, a volume per unit of length $V_A/L$ which is smaller than a corresponding volume per unit of length $V_D/L$ of the donor channel 2.

FIG. 4 shows a chromatography system 14 comprising a dialysis cell 1 according to the invention. In said system 14, a sample solution, which is also referred to here as donor solution, is provided in a sample container 15. The donor solution is pumped by means of a pump 16 through the first half-cell 6 of the dialysis cell 1 and then collected in a collection container 17 for the purpose of disposal. An acceptor solution is provided in an acceptor container 18 and is pumped by means of a further pump 16' through the second half-cell 7 of the dialysis cell 1. Excess acceptor solution is likewise collected in a collection container 17' for the purpose of disposal. As has already been elucidated above, a so-called stopped-flow dialysis is carried out by stopping the flow of the acceptor solution, also referred to here as acceptor flow, through the half-cell 7 while continuing the flow of the donor solution, also referred to here as donor flow, through the half-cell 6. This is maintained until the acceptor solution within the half-cell 7 has a desired minimum proportion of the concentration of the analyte in the donor solution within the half-cell 6. Such a minimum proportion can, for example, be 90%, 95% or 99%.

After dialysis has been carried out, the injection valve 19 can be switched, the result being that the analyte is supplied to the chromatography column 20. While the analyte is supplied to the chromatography column 20, the donor flow is stopped. The actual chromatography part of the chromatography system 14 is depicted here in a highly simplified manner. An eluent is provided in a eluent container 21 and is pumped by means of a pump 16''', especially a high-pressure pump, through the separation column 20 via the injection valve 19. After detection has been carried out by means of the detector 22, the sample separated by ion chromatography is likewise collected in a collection container 17'' for the purpose of disposal. However, it is self-evident that so-called tandem techniques, for example a coupling of a conductivity detector and a mass spectrometer (MS), are realizable too in the context of the present invention.

Figure 5:
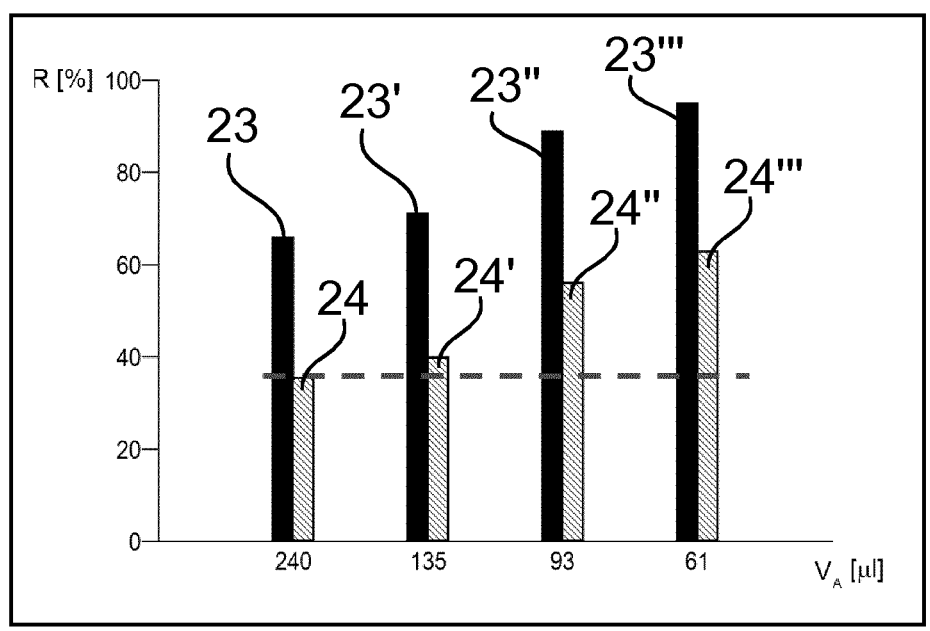
FIG. 5: Influence of the volume $V_A$ of the acceptor channel on the recovery rate R.

FIG. 5 shows the influence of the volume $V_A$ of the acceptor channel on the recovery rate R. The bars 23, 23', 23'', 23''' each depict the observed values for chloride, whereas the bars 24, 24', 24'', 24''' represent data for sulfate. The depicted values each show the recovery rate R after a dialysis time $t_D$ of 2 min. For all the measurements, a donor channel having a depth of 515 μm and a volume $V_D$ of 240 μl was used. Acceptor channels having volumes $V_A$ of 240 μl, 135 μl, 93 μl and 61 μl were tested. It can be seen that the recovery rate R becomes higher with decreasing volume $V_A$ of the acceptor channel while the dialysis time $t_D$ remains the same.

Figure 6:
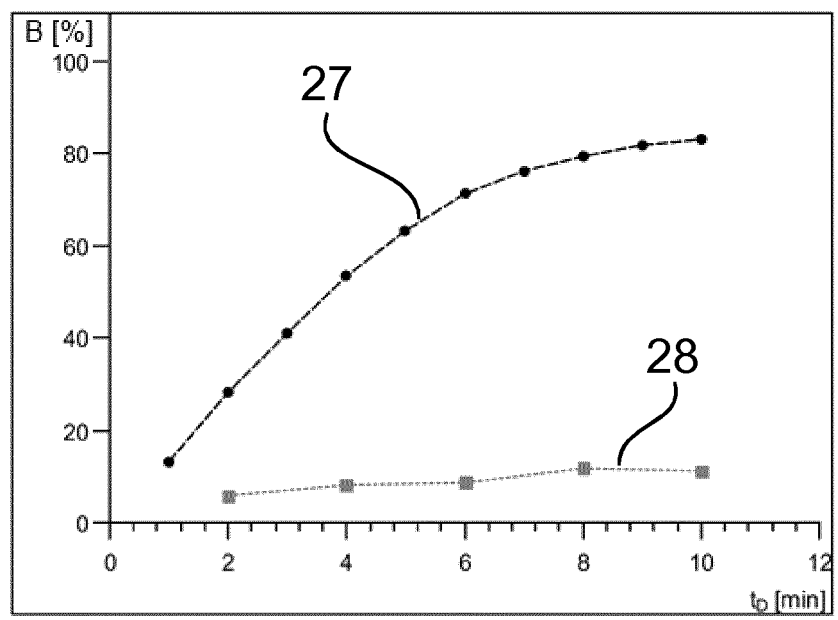
FIGS. 6 and 7: Comparison of a dialysis cell according to the invention with such a dialysis cell from the prior art with respect to the breakthrough of lignins.
Figure 7:
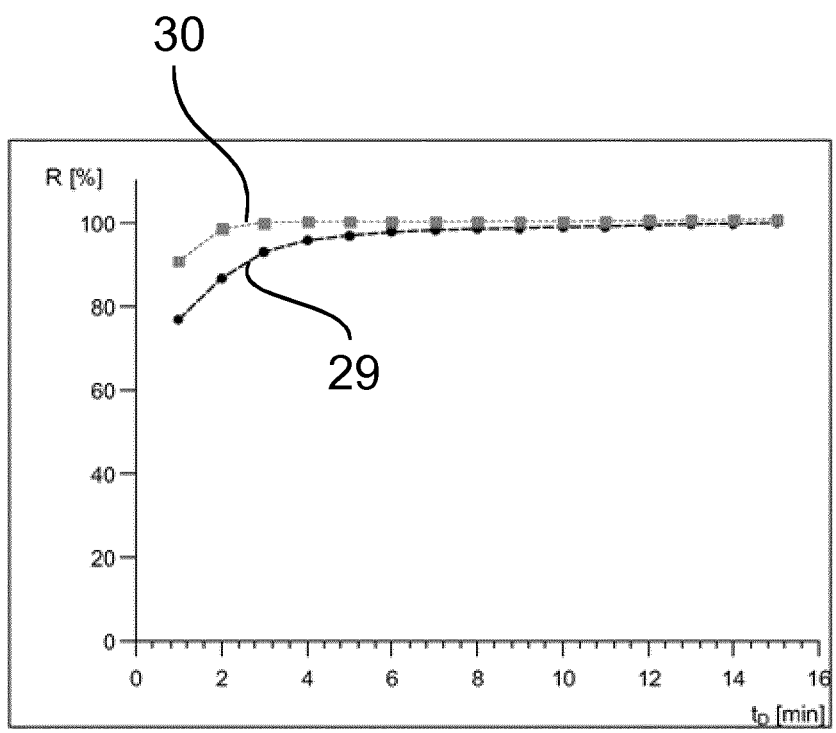

FIGS. 6 and 7 show a comparison of a dialysis cell according to the invention with such a dialysis cell from the prior art with regard to the breakthrough of matrix molecules. In this connection, a sample having a concentration of lignin of 25 mg/l was prepared. The lignin concentration was determined using a UV detector at a wavelength of 274 nm. The graph 27 shows the breakthrough rate B of lignin as a function of the dialysis time $t_D$ for a symmetrical dialysis cell having a donor channel depth and acceptor channel depth of 515 μm, a donor channel volume $V_D$ and acceptor channel volume $V_A$ of 240 μl and a cellulose acetate membrane having a pore size of 0.2 μm. It is evident that the breakthrough rate B is above 70% after a dialysis time $t_D$ of 4 min. In contrast, as shown in graph 28, the breakthrough rate B for an asymmetrical dialysis cell having a donor channel depth of 515 μm, a donor channel volume $V_D$ of 240 μl, an acceptor channel depth of 515 μm, an acceptor channel volume $V_A$ of 90 μl and a polycarbonate membrane having a 0.1 μm pore size increases significantly more slowly over the period of dialysis and only reaches precisely a value of 10% even with a dialysis time $t_D$ of 10 min.

FIG. 7 shows the recovery rate R of nitrate as a function of the dialysis time $t_D$ for the dialysis configurations shown in FIG. 6. Graphs 29 and 30 show the recovery rates R of nitrate corresponding to graphs 27 and 28, respectively, in FIG. 6. It is evident from FIG. 7 that the reduced matrix breakthrough as shown in FIG. 6 for asymmetrical dialysis with a fine-pored membrane is present even when the equilibration time $t_A$ is lower for asymmetrical dialysis with a fine-pored membrane than for symmetrical dialysis with a coarse-pored membrane.

FIGS. 6 and 7 show that, through the use of an asymmetrical dialysis cell as opposed to a symmetrical dialysis cell, it is possible, by choosing suitable membranes, to reduce the equilibration time $t_A$ for the analyte and to reduce the matrix breakthrough at the same time.

An application example of a dialysis cell 1 according to the invention is provided below and by FIGS. 8 and 9. Specifically, the nitrate and sulfate content of water samples from the Britzer Kirchteich (Berlin, Germany) was ascertained. What is concerned here is a surface water exhibiting signs of eutrophication and having a high content of humic substances. Altogether five water samples were collected and the concentration of said anions was determined by ion chromatography. The sample preparation was carried out by means of stopped-flow dialysis.

Use was made of two different dialysis cells which both had a structure corresponding to that shown in FIG. 1. The first dialysis cell was a dialysis cell known from the prior art, in which both the donor channel and the acceptor channel had a depth of 515 μm and a volume $V_A$ and $V_D$, respectively, of 240 μl. The second dialysis cell was a dialysis cell according to the invention, wherein the donor channel likewise had a depth of 515 μm and a volume $V_D$ of 240 μl. The acceptor channel had a depth of only 210 μm and a volume $V_A$ of 90 μl.

In both cases, a membrane composed of mixed cellulose ester and having a pore diameter of 0.05 μm (Merck Millipore) was used. Because of the small pore size, said membrane is distinguished by a high level of retention with respect to potentially interfering substances, especially macromolecular substances, such as, for example, humins or lignins.

Figure 8:
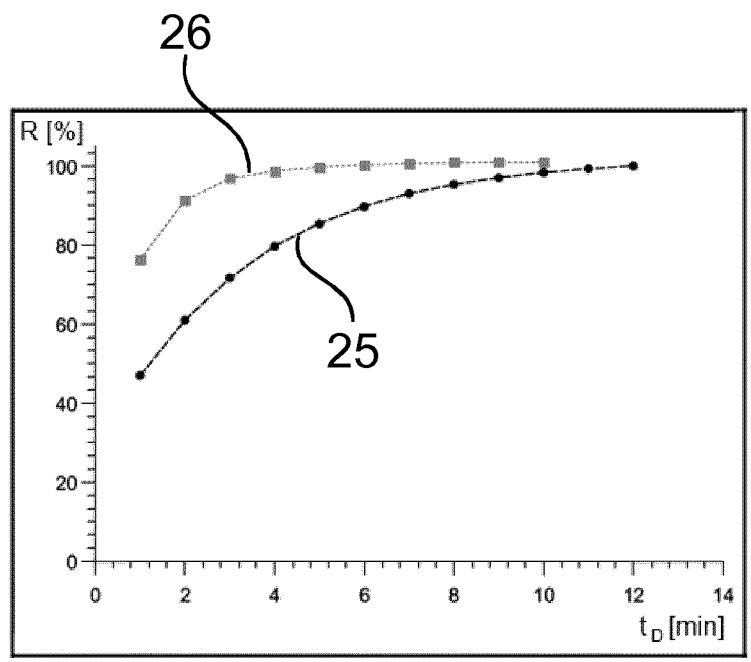
FIGS. 8 and 9: Example of a sample treatment using a dialysis cell according to the invention.
Figure 9:
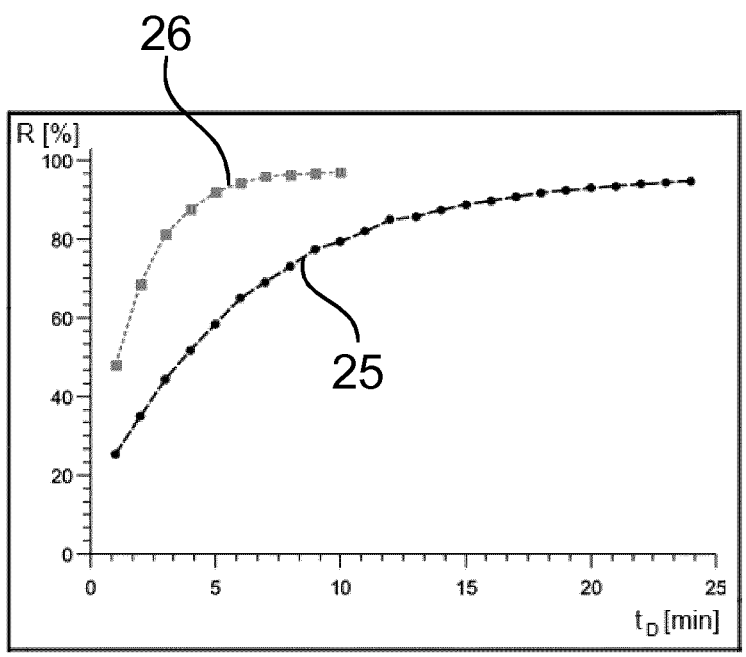

As shown by FIGS. 8 and 9, a dialysis time $t_D$ required both for nitrate and for sulfate was determined as a preliminary experiment. For this purpose, standard solutions having a concentration of 5 mg/l were prepared and dialyzed for each ion. FIG. 8 shows the results for the anion nitrate. The graph 25 represents the recovery rate R for an acceptor channel having a volume $V_A$ of 240 µl. The graph 26 represents the corresponding recovery rate R for an acceptor channel having a volume $V_A$ of 90 µl. It can be seen that, in the case of the asymmetrical dialysis cell, there is a recovery rate R of over 90% for nitrate even with a dialysis time $t_D$ of 2 min. By contrast, in the case of the symmetrical dialysis cell, this value is achievable only with a dialysis time $t_D$ of over 6 min. FIG. 9 shows an analogous picture for the anion sulfate. It can be seen here that a recovery rate R of 90% is achieved with the asymmetrical dialysis cell with a dialysis time $t_D$ of approx. 5 min, whereas a corresponding value in the case of the symmetrical cell structure can be achieved only with a dialysis time $t_D$ of over 15 min. The following table combines the results of these preliminary experiments for nitrate and sulfate and for further anions.

|  | Dialysis time $t_D$ [min] | Recovery rate R [%] | Sample consumption [ml] | Dialysis time $t_D$ [min] | Recovery rate R [%] | Sample consumption [ml] |
| --- | --- | --- | --- | --- | --- | --- |
|  | 240 µl acceptor channel (515 µm depth) | | | 90 µl acceptor channel (210 µm depth) | | |
| $F^-$ | 15 | 97.2 | 11.6 | 6 | 98.3 | 5.4 |
| $Cl^-$ | 9 | 97.1 | 7.5 | 4 | 99.0 | 4.1 |
| $NO_2^-$ | 11 | 98.2 | 8.8 | 4 | 98.5 | 4.1 |
| $Br^-$ | 9 | 98.4 | 7.5 | 3 | 98.3 | 3.4 |
| $NO_3^-$ | 9 | 97.1 | 7.5 | 3 | 98.8 | 3.4 |
| $SO_4^{2-}$ | 24 | 94.8 | 16.3 | 8 | 96.4 | 6.8 |

As can be gathered from the table above, it was possible to achieve shorter dialysis times CD with the asymmetrical dialysis cell 1 for all the anions tested. The recovery rates R achieved were in the same range as for a symmetrical dialysis cell or were often even higher. Furthermore, it was fundamentally possible to achieve a lower sample consumption with an asymmetrical structure of the dialysis cell.

The following table combines the nitrate and sulfate contents for the abovementioned surface water analysis.

| | $NO_3^-$ | | $SO_4^{2-}$ | |
| --- | --- | --- | --- | --- |
| Sample number | Concentration [mg/l] | RSD [%] | Concentration [mg/l] | RSD [%] |
| 1 | 0.317 | 4.7 | 3.74 | 1.1 |
| 2 | 0.099 | 4.6 | 3.80 | 0.5 |
| 3 | 0.132 | 4.4 | 3.84 | 0.6 |
| 4 | 0.068 | 6.5 | 3.85 | 1.3 |
| 5 | 0.074 | 1.7 | 3.83 | 0.2 |

Besides the concentration value for each individual sample, the relative standard deviation (RSD) of the concentration is additionally reported.

In summary, it can be stated that distinctly shorter dialysis times $t_D$ and thus a higher sample throughput can be achieved with a dialysis cell 1 according to the invention having an asymmetrical structure. Furthermore, it was established that the amount of sample required can be reduced by at least a factor of 2 with such a dialysis cell 1. Furthermore, the shorter time during which the matrix is in contact with the dialysis membrane 4 reduces the undesired breakthrough of matrix constituents and associated adverse effects on the ion chromatography system.

Figure 10:
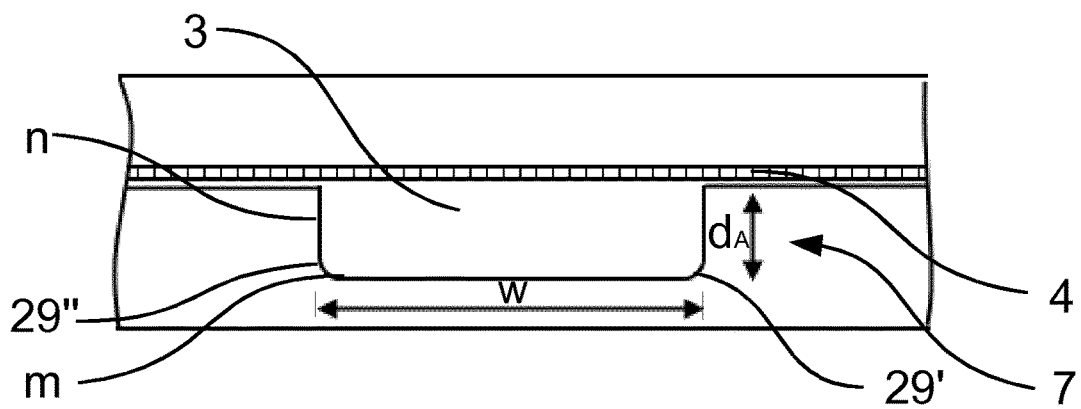
FIGS. 10 and 11: Cross sections through an acceptor channel of a dialysis cell according to the invention with and without support elements.

FIG. 10 shows a cross section through an acceptor half-cell 7 according to the invention, containing an acceptor channel 3. The cross section through the acceptor channel 7 is formed as a rectangle having rounded corners 29', 29" on the side m that faces away from the membrane. The ratio of the width w of the side bounded by the membrane 4 to the depth $d_A$ of the rectangle shown in cross section is not shown true to scale. The same applies to the radius of curvature r. According to the invention, the ratio of the width w of the side bounded by the membrane to the depth $d_A$ of the rectangle shown in cross section is from 80:1 to 10:1, particularly preferably from 40:1 to 15:1 and very particularly preferably from 25:1 to 20:1. The radius of curvature of the arc-shaped section, which connects the section m of the acceptor channel 3 that is opposite the dialysis membrane to the lateral boundaries of the acceptor channel 3 that are attached to the dialysis membrane, is between 0.05 and 1 mm, preferably between 0.1 and 0.8 mm and particularly preferably between 0.2 and 0.4 mm. The channel configuration shown minimizes the ratio of the fluid volume per section to the contact surface with the membrane 4 in the same section. Moreover, what is prevented during fluid flow is the deposition of acceptor solution in the corners 29', 29" of the cross section that face away from the membrane 4.

Figure 11:
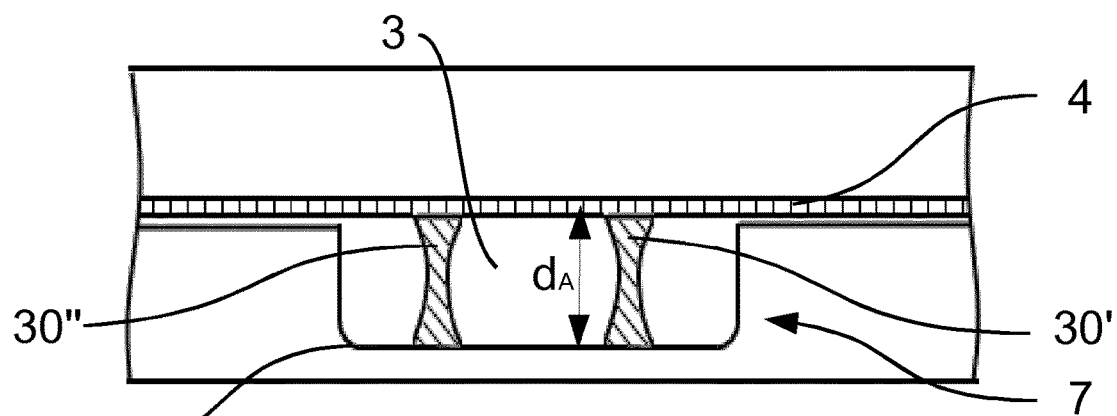

FIG. 11 shows a cross section through an acceptor half-cell 7 according to the invention, containing an acceptor channel 3 in which multiple support elements 30', 30" are mounted, which support elements space the membrane 4 from the side m of the acceptor channel 3 that faces away from the membrane. The support elements 30', 30" have the height $d_A$, which corresponds to the depth of the acceptor channel 3. The support elements are designed here as waisted cylinders in order to obstruct the fluid flow as little as possible and, at same time, to provide the membrane 4 with support that is as solid as possible. The broadening of size toward the membrane reduces the risk that the membrane 4 might be perforated by a conically tapering cylinder end or a conical design of the support element 30', 30".

Figure 12:
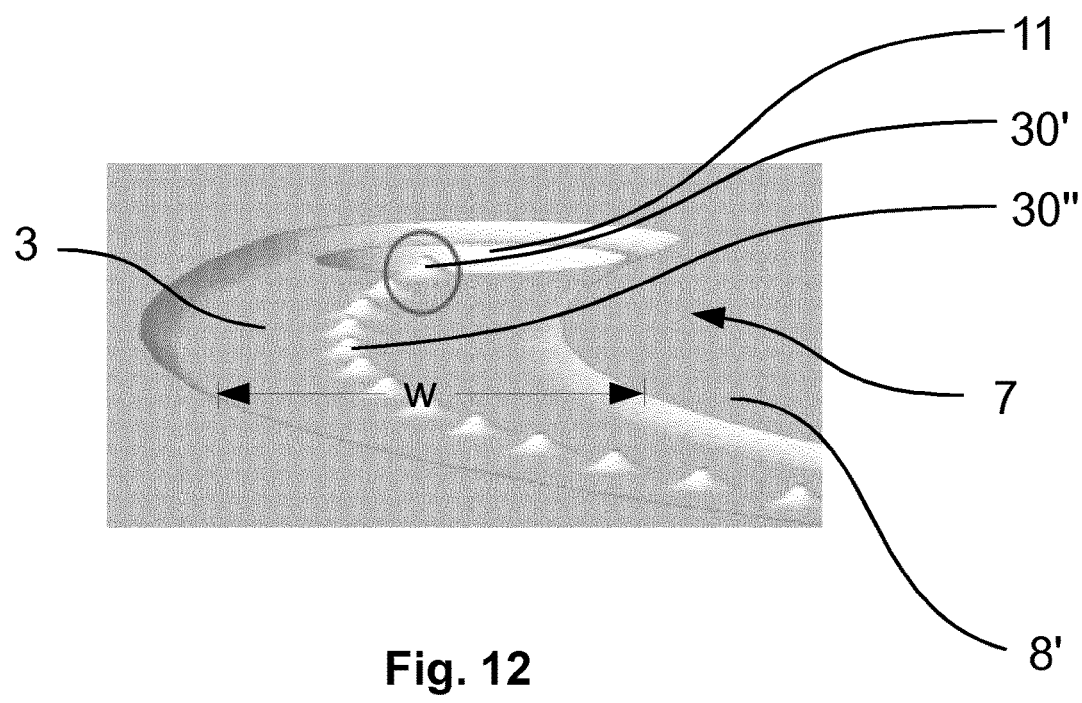
FIG. 12: Perspective view of an acceptor channel of a dialysis cell according to the invention.

FIG. 12 shows a perspective view of an acceptor half-cell 7 according to the invention, containing an acceptor channel 3. Here, the support elements are curved concavely in the shape of a cone. The support elements 30', 30" are integrally formed with the acceptor channel 3. The support elements 30', 30" are arranged centrally in the width m of the acceptor channel 3. The distance between every two adjacent support elements is constant over the channel length. A supply line 11 for an acceptor solution is also shown. The support element 30' is near the supply line 11 in order to prevent the membrane 4 (not shown) from resting on the walls and/or the base of the acceptor channel 3 even and specifically at the supply line opening 11.

Figure 13:
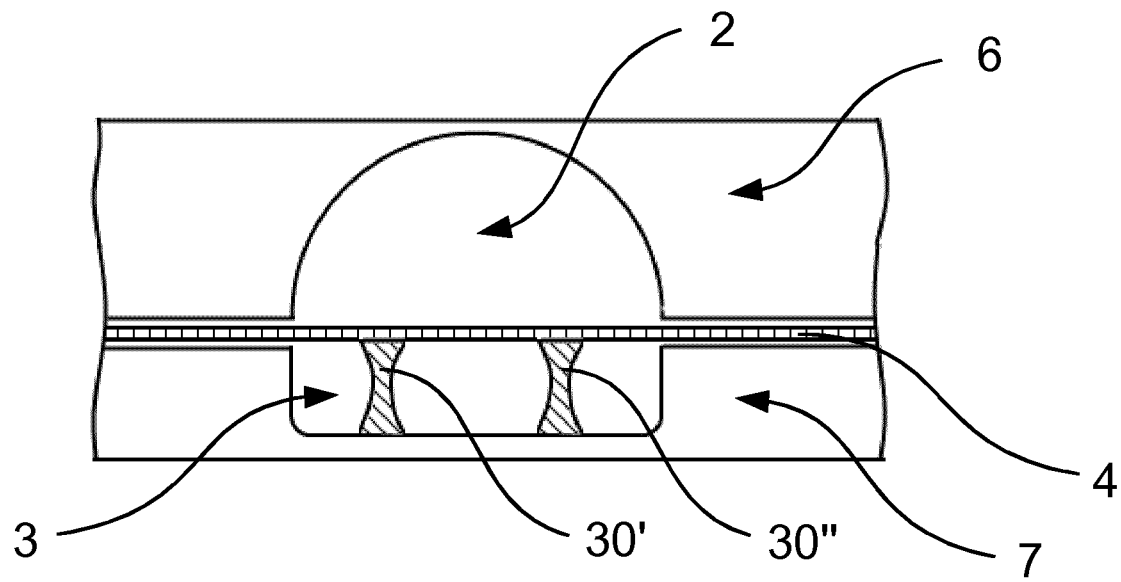
FIGS. 13 and 14: Cross sections through two alternative arrangements of two half-cells of a dialysis cell according to the invention, with support elements in each case.
Figure 14:
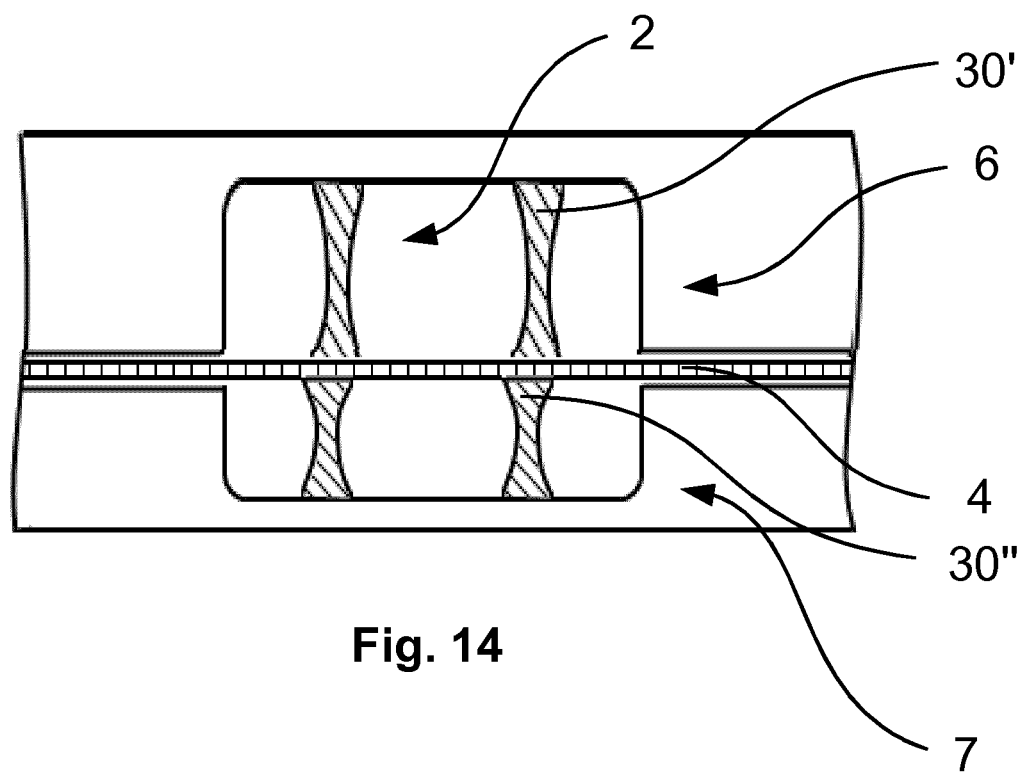

FIGS. 13 and 14 each show a cross section through an arrangements of, in each case, two half-cells of a dialysis cell according to the invention in the assembled state, with support elements 30', 30" in each case. In FIG. 13, the donor half-cell 6 comprising the donor channel 2 is designed such that the cross section shows a semicircle. The acceptor cell 7 comprising the acceptor channel 3 is designed as already described for FIGS. 10 to 12. In FIG. 14, support elements 30', 30" are formed both in the donor channel 2 and in the acceptor channel 3. Although this is not preferred, it is nevertheless part of the invention.

Figure 15:
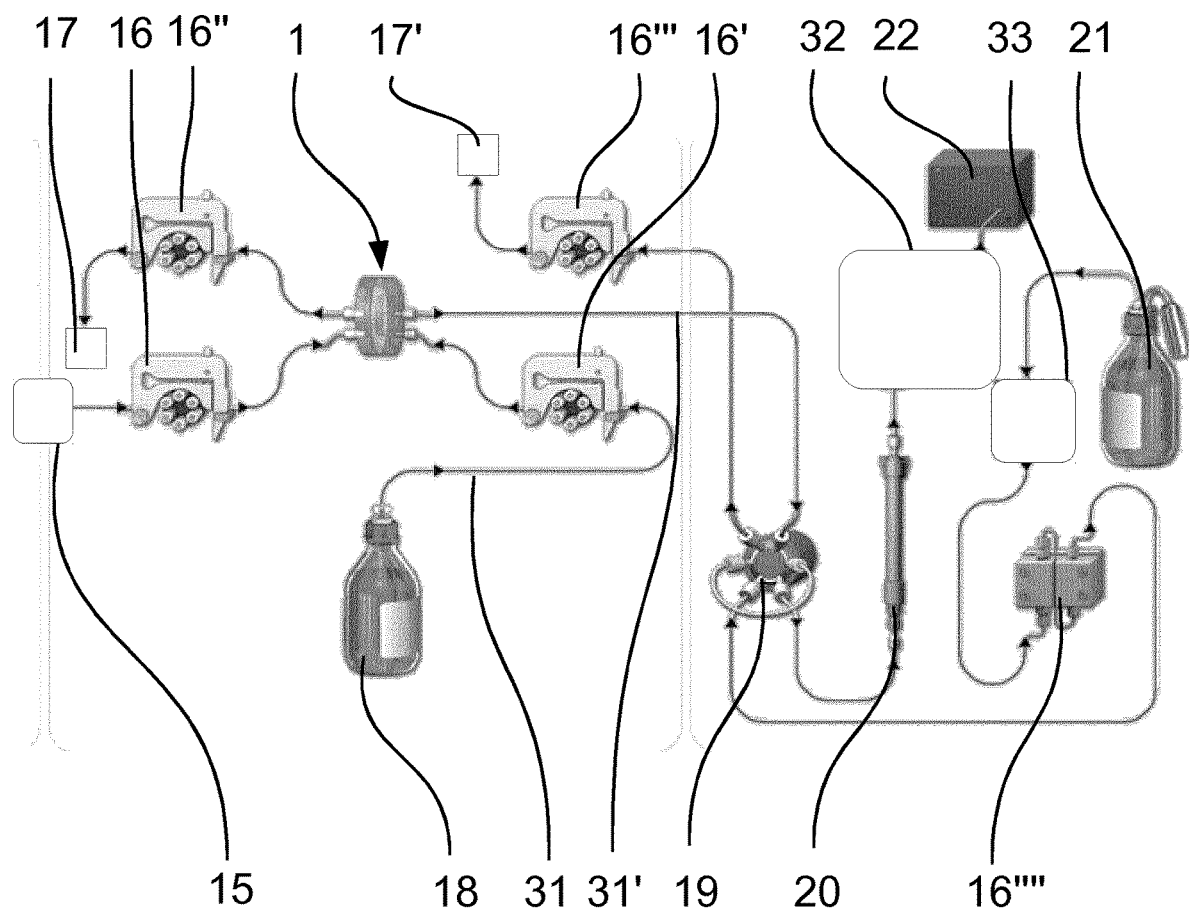
FIG. 15: Schematic representation of a device for sample preparation for a chemical analytical method in a dialysis process.

FIG. 15 shows a schematic representation of a device for sample preparation for a chemical analytical method in a dialysis process. As in FIG. 4, the system comprises a dialysis cell 1 according to the invention. The donor solution in the sample container 15 is pumped by means of a pump 16 through the first half-cell of the dialysis cell 1 and then conducted through the pump 16" to a collection container 17. The acceptor solution in the acceptor container 18 is pumped by means of a further pump 16' through the second half-cell of the dialysis cell 1. Excess acceptor solution is likewise collected in a collection container 17' for the purpose of disposal. The forwarding of the acceptor solution to the collection container 17' is additionally driven by the pump 16'''.

The stopped-flow method corresponds to the method described in relation to FIG. 4. In addition, the system is configured such that the flow in the donor circuit is stopped while either excess acceptor solution is supplied to the collection container 17' or the acceptor solution containing the predetermined analyte concentration is supplied to an analytical method.

This ensures that always at most one of the two half-cells of the dialysis cell 1 exhibits a flow. In other words, the pumps 16, 16", on the one hand, and the pumps 16' and 16''', on the other, are operated in an alternating manner. During the dialysis time $t_D$, only the pumps of the donor circuit are operated and, after expiration of the dialysis time $t_D$, only the pumps of the acceptor circuit are operated.

Switching of the injection valve 19 determines whether the acceptor liquid is supplied to the collection container 17' or to the chromatography column 20. The actual chromatography part of the chromatography system can comprise an eluent degasser 33 in addition to the eluent container 21 and the high-pressure pump 16"". Before the detection in the detector 22, the chromatographically separated sample can pass through at least one suppressor module 32.

Although not shown, what is also part of the invention is that the pump 16 and the pump 16" are combined in a two-channel pump, preferably a peristaltic two-channel pump. This ensures that inflow and outflow of the donor liquid into/out of the donor half-cell are determined by the same stroke movement and synchronized as a result. Additionally or alternatively, the pumps 16' and 16''' of the acceptor circuit can be designed as a two-channel pump, especially as a peristaltic two-channel pump, with the result that inflow and outflow of the acceptor liquid into/out of the acceptor half-cell are determined by the same stroke movement and synchronized as a result. Such an embodiment prevents pressure fluctuations in the respective half-cells.

What is further part of the invention is that the capillary 31 connecting the acceptor solution container 18 to the acceptor half-cell via the pump 16' and the second capillary 31' connecting the acceptor half-cell to the injection valve 19 are designed such that the diameter of the capillary comprises at most 0.5 mm.

The invention claimed is:

1. A dialysis cell for sample preparation for a chromatographic method comprising:
   a donor channel; and
   a parallelly running acceptor channel,
   wherein, when used as intended, the donor channel and the acceptor channel are separated from one another by a selectively permeable dialysis membrane,
   wherein the acceptor channel has, on its entire length, a volume $V_A$ which is smaller than a parallelly running volume $V_D$ of the donor channel,
   wherein the donor channel and the acceptor channel are spiral or meandering,
   wherein the dialysis cell comprises two half-cells, between which the dialysis membrane is arranged, wherein the donor channel and the acceptor channel are formed as, in each case, an indentation in a contact surface of one of the half-cells with the dialysis membrane, and
   wherein at least one support element is formed in the acceptor channel, which support element spaces the dialysis membrane from the side of the acceptor channel that faces away from the dialysis membrane.

2. The dialysis cell as claimed in claim 1, wherein the acceptor channel has at least one length section along the length thereof having a volume per unit of length $V_A/L$ of from 0.005 mm$^3$/mm to 2.0 mm$^3$/mm.

3. The dialysis cell as claimed claim 1, wherein the donor channel has at least one length section along a length thereof having a volume per unit of length $V_D/L$ of from 0.25 mm$^3$/mm to 3.5 mm$^3$/mm.

4. The dialysis cell as claimed in claim 1, wherein the dialysis membrane has a pore size of from 0.01 μm to 1.0 μm.

5. The dialysis cell as claimed in claim 1, wherein the dialysis membrane consists of a material selected from a list consisting of cellulose acetate, cellulose nitrate, polyvinylidene fluoride, polycarbonate, mixed cellulose ester, cellulose hydrate, regenerated cellulose, and polyamide.

6. The dialysis cell as claimed in claim 1, wherein the cross section through the acceptor channel is, at least sectionally, a rectangle having rounded corners on the side facing away from the dialysis membrane, wherein the ratio of the width of the side bounded by the dialysis membrane to the depth of the cross section through the acceptor channel is from 80:1 to 10:1.

7. An analytical system comprising a dialysis cell (1) according to claim 1.

8. The dialysis cell as claimed in claim 1, wherein the cross section through the acceptor channel is, at least sectionally, a rectangle having rounded corners on the side facing away from the dialysis membrane, wherein the rounded corners have a radius of curvature of from 0.05 mm to 1 mm.

9. A device for sample preparation for a chromatographic method in a dialysis process comprising a dialysis cell, wherein at least one of the following applies:
   that a donor circuit has a first pump device which conveys a donor liquid to the dialysis cell and has a second pump device which conveys the donor liquid away from the dialysis cell; and
   that an acceptor circuit has a first pump device which conveys an acceptor liquid to the dialysis cell and has a second pump device which conveys the acceptor liquid away from the dialysis cell,
   wherein the device comprises a dialysis cell according to claim 1.

10. The analytical system according to claim 7, wherein the system is an ion chromatography system (IC), a system for high-performance liquid chromatography (HPLC), a capillary electrophoresis system (EC) or a mass spectrometry system (MS).

* * * * *